United States Patent
Beckmann et al.

(12) 
(10) Patent No.: US 6,306,615 B1
(45) Date of Patent: Oct. 23, 2001

(54) DETECTION METHOD FOR MONITORING β TUBULIN ISOTYPE SPECIFIC MODIFICATION

(75) Inventors: Holger Beckmann, El Cerrito; Edit Santha, Cupertino, both of CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

(21) Appl. No.: 09/377,554

(22) Filed: Aug. 19, 1999

(51) Int. Cl.[7] .............................. C12Q 1/00; G01N 33/53; G01N 33/567; G01N 33/574; G01N 33/555
(52) U.S. Cl. .............................. 435/7.2; 435/4; 435/7.1; 435/7.21; 435/7.23; 435/7.24; 435/7.25; 435/7.7; 435/7.92; 435/325; 435/326; 435/327; 435/328; 435/329; 435/330; 435/331; 435/332; 435/343; 435/344; 530/350; 530/380; 530/385; 530/387.1; 530/387.3; 530/387.7; 530/387.9; 530/388.1; 530/388.15; 530/388.2; 530/391.3; 530/391.5
(58) Field of Search .............................. 435/4, 7.1, 7.21, 435/7.24, 7.7, 7.92, 7.23, 7.25, 325, 326, 327, 328, 329, 330, 331, 332, 343, 344; 530/388.1, 388.15, 388.2, 350, 380, 385, 387.1, 387.3, 387.7, 387.9, 391.3, 391.5

(56) References Cited

U.S. PATENT DOCUMENTS 5,880,151 3/1999 Medina et al. ..................... 514/518

FOREIGN PATENT DOCUMENTS

| | | | |
|---|---|---|---|
| WO 97/30677 | 8/1997 | (WO) . | |
| WO 98/05315 | 2/1998 | (WO) | ............ A61K/31/165 |
| WO 99/00671 * | 1/1999 | (WO) . | |
| WO 99/10320 | 3/1999 | (WO) | ............ C07C/311/21 |
| WO 00/50593 * | 8/2000 | (WO) . | |
| WO 00/56894 * | 9/2000 | (WO) . | |

OTHER PUBLICATIONS

Shan, B. et al., "Selective, covalent modification of β–tubulin residue Cys–239 by T138067, an antitumor agent with in vivo efficacy against multidrug–resistant tumors," *Proc. Natl. Acad. Sci. USA*, 96:5686–5691 (1999).

Draberova et al. Expression of class III Beta–tubulin in normal and neoplastic humum tissues. Histochem Cell. Biol. 109:231–239, Mar. 1998.*

Harlow and Lane. Antibodies, A Laboratory Manual, Chapter 9, 1988.*

Modig et al. "Identification of beta.III and beta.IV tubulin isotypes in cold–adapted microtubules from Atlantic cod (Gadus murhua): antibody mapping and cDNA sequencing, "Cell Motil. Cytoskeleton 42(4):315–330, 1999.*

Sharma et al., "Use of N,N'–polymethylenebis (iodoacetamide) derivatives as probes for the detection of conformational differences in tubulin isotypes, "Journal of Protein Chemistry 13(2): 166, 1994.*

* cited by examiner

*Primary Examiner*—Sheela Huff
*Assistant Examiner*—Alana M. Harris
(74) *Attorney, Agent, or Firm*—Townsend and Townsend and Crew LLP

(57) ABSTRACT

This invention relates to monoclonal antibodies that recognize modified β-tubulin isotypes, methods of using such antibodies to detect modified β-tubulin isotypes, methods of using such antibodies to monitor β-tubulin modifying agents administered to a patient, methods of using such antibodies to isolate modified β-tubulin, and methods of detecting the anti-modified β-tubulin antibodies.

17 Claims, 6 Drawing Sheets cmpd 1-modified β2-tubulin peptide

| clone | 1F6D8 | 1B2C11 | 3A1C11 | 1F6A11 | 2C1H7 | 5F1D4 | 3F2A4 | 5F5C11 | 6D4D11 | 3F2D2 | 5F5E4 | 6D4G4 |
|---|---|---|---|---|---|---|---|---|---|---|---|---|
| OD$_{405/490}$ | 1.445 | 0.970 | 1.425 | 2.020 | 1.325 | 1.750 | 1.395 | 1.682 | 1.345 | 0.086 | 1.696 | 1.541 |
| clone | 3D12D1 | 4B6G6 | 6H8E3 | 3D12D6 | 4B6E1 | 6H8G2 | 3E10A3 | 6E7G1 | 6A7F9 | 3E10G10 | 6E7F4 | 6H10C7 |
| OD$_{405/490}$ | 1.145 | 1.019 | 1.825 | 1.050 | 1.132 | 1.539 | 0.538 | 0.854 | 1.618 | 0.618 | 1.340 | 1.259 |
| clone | 3A1G1 | 5F1D4 | 6D4D11 | 3F2A4 | 6H8E3 | NONE | | | | | | |
| OD$_{405/490}$ | 1.546 | 1.721 | 1.662 | 1.487 | 1.675 | 0.261 | | | | | | | unmodified β2-tubulin peptide

| clone | 1F6D8 | 1B2C11 | 3A1C11 | 1F6A11 | 2C1H7 | 5F1D4 | 3F2A4 | 5F5C11 | 6D4D11 | 3F2D2 | 5F5E4 | 6D4G4 |
|---|---|---|---|---|---|---|---|---|---|---|---|---|
| OD$_{405/490}$ | 0.212 | 0.195 | 0.346 | 0.654 | 0.158 | 1.319 | 0.220 | 0.318 | 0.323 | 0.294 | 0.452 | 0.252 |
| clone | 3D12D1 | 4B6G6 | 6H8E3 | 3D12D6 | 4B6E1 | 6H8G2 | 3E10A3 | 6E7G1 | 6A7F9 | 3E10G10 | 6E7F4 | 6H10C7 |
| OD$_{405/490}$ | 0.755 | 0.922 | 1.202 | 0.290 | 0.752 | 1.013 | 1.180 | 1.480 | 1.980 | 1.133 | 1.777 | 1.701 |
| clone | 3A1G1 | 5F1D4 | 6D4D11 | 3F2A4 | 6H8E3 | NONE | | | | | | |
| OD$_{405/490}$ | 0.272 | 1.267 | 0.475 | 0.250 | 1.326 | 0.174 | | | | | | |

FIG. 2A.

|  | Hybridoma clone | Ig isotype | Specificity |
|---|---|---|---|
| Class 1 | 1F6D8<br>1B2C11<br>3A1C11<br>2C1H7<br>3F2A4<br>5F5C11<br>6D4D11 | IgG$_{2b}$/κ<br>IgG$_{2b}$/κ<br>IgG$_1$/κ<br>IgG$_1$/κ<br>IgG$_1$/κ<br>IgG$_1$/κ<br>IgG$_1$/κ | cmpd 1-modified β2-tubulin peptide<br>and<br>cellular cmpd 1-modified β-tubulin |
| Class 2 | 3D12D1<br>4B6G6<br>5F1D4<br>6H8E3<br>6H10C7 | IgM/κ<br>IgM/κ<br>IgM/κ<br>IgG$_{2a}$/κ<br>IgG$_{2b}$/κ | cmpd 1-β2-tubulin peptide<br>and<br>unmodified β2-tubulin peptide |
| Class 3 | 3E10A3<br>6A7F9<br>6E7G1 | IgG$_1$/κ<br>IgG$_{2b}$/κ<br>IgG$_{2a}$/κ | unmodified β2-tubulin peptide |

*FIG. 2B.*

Detection

Monoclonal Ab
2C1H7

Polyclonal Ab
α/β-tubulin

Autoradiogram

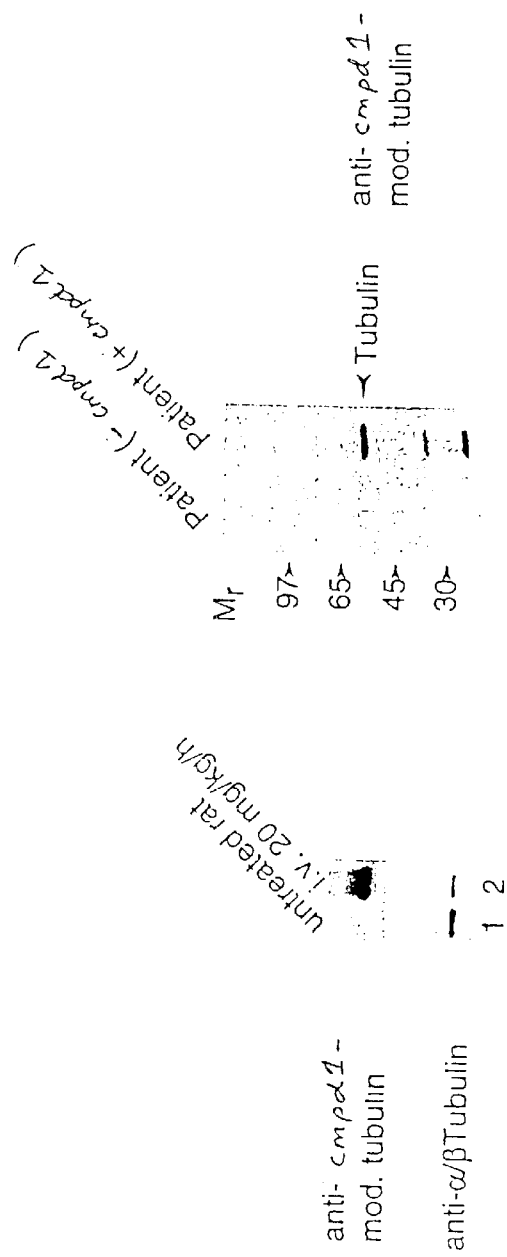
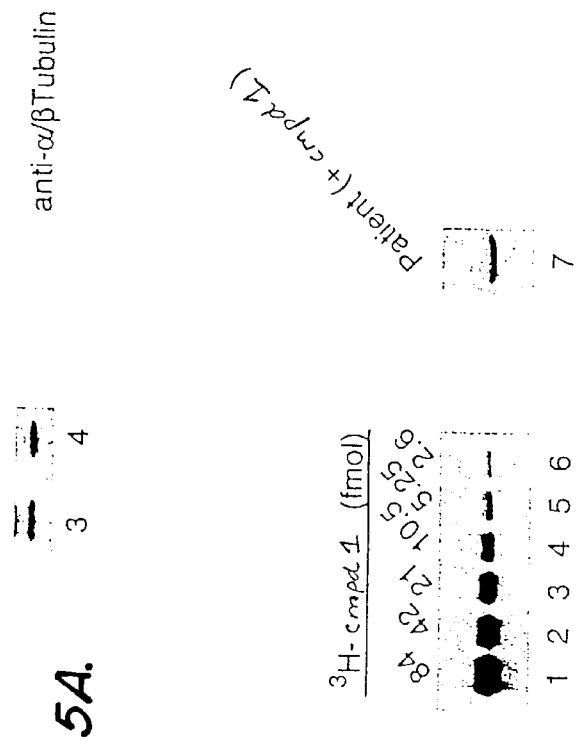
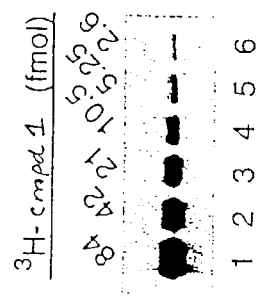
FIG. 5A.
FIG. 5B.

DETECTION METHOD FOR MONITORING β TUBULIN ISOTYPE SPECIFIC MODIFICATION

CROSS-REFERENCES TO RELATED APPLICATIONS

The present application is related to U.S. Pat. No. 5,880,151, issued Mar. 9, 1999; PCT 97/02926, filed Feb. 22, 1997; PCT 97/12720, filed Jul. 18, 1997; PCT 98/16781, filed Aug. 13, 1998; PCT 99/13759, filed Jun. 16, 1999; and PCT 99/16032, filed Jul. 15, 1999, herein each incorporated by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to monoclonal antibodies that recognize modified β-tubulin, methods of using such antibodies to detect modified β-tubulin, methods of using such antibodies to monitor β-tubulin modifying agents administered to a patient, methods of using such antibodies to isolate modified β-tubulin, and methods of detecting the anti-modified β-tubulin antibodies.

BACKGROUND OF THE INVENTION

Microtubules are composed of α/β-tubulin heterodimers and constitute a crucial component of the cell cytoskeleton. Furthermore, microtubules play a pivotal role during cell division, in particular when the replicated chromosomes are separated during mitosis. Interference with the ability to form microtubules from α/β-tubulin heterodimeric subunits generally leads to cell cycle arrest. This event can, in certain cases, induce programmed cell death. Thus, natural products and organic compounds that interfere with microtubule formation have been used successfully as chemotherapeutic agents in the treatment of various human cancers.

Pentafluorophenylsulfonamidobenzenes and related sulfhydryl and disulfide modifying agents (see, e.g., compound 1; 2-fluoro-1-methoxy-4-pentafluorophenylsulfonamidobenzene; FIG. 1C) prevent microtubule formation by selectively covalently modifying β-tubulin. For example, compound 1 does not covalently modify all of the five known β-tubulin isotypes. Instead, binding is restricted to those β-tubulin isotypes that have a cysteine residue at amino acid position 239 in β-tubulin. Such isotypes include β1, β2 and β4-tubulin. The other two isotypes (β3 and β5) have a serine residue at this particular position (Shan et al., Proc. Nat'l Acad. Sci USA 96:5686–5691 (1999)). It is notable that no other cellular proteins are modified by compound 1.

Although β-tubulin modification can be monitored using the tritiated derivative of compound 1 or other β-tubulin modifying agents, in many cases this method is either impractical or not sensitive enough. Specific, sensitive methods of detecting β-tubulin modification are needed for diagnostic applications and for dose monitoring in patients receiving chemotherapeutic agents that modify β-tubulin.

The present application is related to U.S. Pat. No. 5,880,151, issued Mar. 9, 1999; PCT 97/02926, filed Feb. 22, 1997; PCT 97/12720, filed Jul. 18, 1997; PCT 98/16781, filed Aug. 13, 1998; PCT 99/13759, filed Jun. 16, 1999; and PCT 99/16032, filed Jul. 15, 1999, herein each incorporated by reference in their entirety.

SUMMARY OF THE INVENTION

Thus, the present invention provides monoclonal antibodies that selectively recognize modified β-tubulin and new methods of detecting β-tubulin modification using such monoclonal antibodies. These methods can be used to detect modified β-tubulin in patient samples, to monitor and adjust doses of β-tubulin modifying agents administered to patients, to isolate modified β-tubulin, and to detect anti-modified β-tubulin antibodies.

In one aspect, the present invention provides a monoclonal antibody that specifically binds to modified β-tubulin, the antibody selected from the group consisting of 1F6D8, 1B2C11, 3A1C11, 2C1H7, 3F2A4, 5F5C11, and 6D4D11. The hybridoma cell line 2C1H7, Accession number, PTA-2686, was deposited on Nov. 16, 2000 with American Type Culture Collection, 10801 University Boulevard, Manassas, Va. 20110, USA.

In one embodiment, the antibody is covalently linked to a detectable moiety. In another embodiment, the antibody is covalently linked to a biotin moiety, an iodine moiety, or an enzyme moiety.

In another aspect, the present invention provides a method of detecting in a sample a modified β-tubulin isotype, the method comprising the steps of: (a) providing a sample treated with a β-tubulin modifying agent; (b) contacting the sample with an antibody that specifically binds to a modified β-tubulin isotype; and (c) determining whether the sample contains a modified β-tubulin isotype by detecting the antibody.

In another aspect, the present invention provides a method of monitoring the amount of β-tubulin isotype in a patient treated with a β-tubulin modifying agent, the method comprising the steps of: (a) providing a sample from the patient; (b) contacting the sample with an antibody that specifically binds to a modified β-tubulin isotype; and (c) determining the amount of modified β-tubulin isotype in the patient sample by detecting the antibody and comparing the amount of antibody detected in the patient sample to a standard curve, thereby monitoring the amount of modified β-tubulin isotype in the patient.

In one embodiment, the β-tubulin is modified at cysteine residue 239. In one embodiment, the antibody is a monoclonal antibody. In another embodiment, the antibody is selected from the group consisting of 1F6D8, 1B2C11, 3A1C11, 2C1H7, 3F2A4, 5F5C11, and 6D4D11.

In one embodiment, the method further comprises the step of using a control antibody that recognizes both modified and unmodified β-tubulins. In another embodiment, the antibody is a monoclonal antibody selected from the group consisting of 3D12D1, 4B6G6, 5F1D4, 6H8E3, and 6H10C7.

In one embodiment, the method further comprises the step of using a control antibody that recognizes only unmodified β-tubulins. In another embodiment, the antibody is a monoclonal antibody selected from the group consisting of 3E10A3, 6A7F9, and 6E7G1.

In one embodiment, the step of determining whether the sample contains a modified β-tubulin isotype comprises detecting the antibody in an assay selected from the group consisting of an ELISA assay, a western blot, an immunohistochemical assay, an immunofluorescence assay, and a real time imaging assay. In another embodiment, the step of determining whether the sample contains a modified β-tubulin isotype further comprises quantitating the amount of modified β-tubulin isotype in the sample. In another embodiment, the antibody is bound to a solid substrate.

In one embodiment, the sample is selected from the group consisting of an in vitro tubulin polymerization reaction sample, a cultured cell, and a patient sample. In another embodiment, the patient sample is a blood sample. In another embodiment, the patient sample is from a cancer patient receiving chemotherapy comprising a β-tubulin modifying agent. In another embodiment, the agent is a pentafluorobenzenesulfonamide. In another embodiment, the agent is 2-fluoro-1-methoxy-4-pentafluorophenylsulfonamidobenzene. In another embodiment, the patient sample is from a human patient. In another embodiment, the method further comprises the step of adjusting the dose of β-tubulin modifying agent administered to the patient.

In another aspect, the present invention provides a method of isolating a modified β-tubulin isotype, the method comprising the steps of: (a) providing a sample treated with a β-tubulin modifying agent; (b) contacting the sample with an antibody that specifically binds to a modified β-tubulin isotype; and (c) isolating the modified β-tubulin isotype by isolating the antibody.

In one embodiment, the β-tubulin is modified at cysteine residue 239.

In another aspect, the present invention provides a method of detecting anti-modified β-tubulin antibody, the method comprising the steps of: (a) providing a sample; (b) contacting the sample with a peptide that specifically binds to anti-modified β-tubulin antibody; and (c) detecting the anti-modified β-tubulin antibody.

In one embodiment, the peptide comprises cysteine residue 239. In one embodiment, the peptide is ATMSGVTTCLRFPGQLNA (SEQ ID NO: 1), GTMECVTTCLRFPGQLNA (SEQ ID NO: 2), or KATMSGVTTCLRFPGQLNA (SEQ ID NO: 3). In another embodiment, the peptide is bound to a solid substrate. In another embodiment, the step of detecting the anti-modified β-tubulin antibody comprises an ELISA assay.

BRIEF DESCRIPTION OF THE DRAWINGS

FIG. 2. Specificity of monoclonal antibodies raised against compound 1-modified β-tubulin. (A) ELISA data against compound 1-modified β-tubulin peptide (shown in FIG. 1) and β-tubulin peptide. Measurements were carried out at $OD_{405/490}$. The numbering of the individual clones is indicated. (B) Summary of properties of monoclonal antibodies.

FIG. 5. Monitoring compound 1-tubulin modification in white blood cells ("WBC"). (A) White blood cells isolated from blood of a rat (lane 1), a human (lane 3), a rat exposed to compound 1 at the indicated concentration for three hours (lane 2) or human exposed to compound 1 at the indicated concentration for three hours (lane 4) were separated by SDS-PAGE and separated proteins were subjected to western blot analyses using an antibody (2C1H7) specific to compound 1-modified β-tubulin. The total amount of α/β-tubulin in lanes 1–4 was visualized using anti-α/β-tubulin antibodies. (B) Determination of the level of compound 1-modified β-tubulin in human WBC exposed to compound 1 (Panel A, lane 4). Lanes 2 to 6 contain a two-fold serial dilution of $^3$H-compound 1-modified brain β-tubulin of reaction in lane 1. Brain tubulin had been modified in vitro (see FIG. 4). The concentration of $^3$H-compound 1-modified β-tubulin is indicated above each lane. Lane 7, human WBC sample as shown in Panel A (lane 4). Compound 1-modification was analysed by western blot using an antibody (2C1H7) specific to compound 1-modified β-tubulin.

DETAILED DESCRIPTION OF THE INVENTION

I. Introduction

This invention provides antibodies that specifically recognize modified β-tubulin isotypes, and methods of detecting and isolating modified β-tubulin using such antibodies. In a preferred embodiment, the β-tubulin is modified at cysteine residue 239. In another preferred embodiment, the antibody is a monoclonal antibody. The antibodies are used in assays to detect modified β-tubulin in samples, to monitor amounts of β-tubulin modifying agents in patients who are receiving chemotherapy and if necessary to adjust dosages of the β-tubulin modifying agent, and to isolate modified β-tubulin. Finally, the invention provides methods of detecting anti-modified β-tubulin antibodies, using modified β-tubulin and antigenic fragments thereof. The invention also provides kits for performing the methods of the invention.

Preferred assays of the invention include an ELISA assay, a western blot, an immunohistochemical assay, an immunofluorescence assay, and a real time imaging assay. Samples in which modified β-tubulin is detected include in vitro polymerization assays treated with a β-tubulin modifying agent, cultured cells treated with a β-tubulin modifying agent, and blood and tissue samples from mammalian subjects, preferably humans, who have been treated with a β-tubulin modifying agent. Optionally, the β-tubulin modifying agent is labeled with a detectable moiety, e.g., tritiated. Using the assays of the invention, the amount of modified β-tubulin in a sample can be quantitated. Preferably, when the amount of modified β-tubulin is quantitated, it is compared to a standard curve of known amounts of modified β-tubulin in a sample.

Figure 1A:
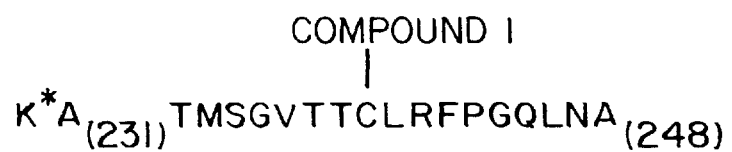
FIG. 1. (A) Shown is the sequence in single letter code of a human β2-tubulin derived peptide (amino acids 231 to 248) bound to compound 1 via Cys239 of β2-tubulin (SEQ ID NO: 4). The amino acid K (*) is not part of the natural β-tubulin sequence. (B) Schematic presentation of the binding mechanism of compound 1 to Cys239 of β2-tubulin. (C) The chemical structure of compound 1 (2-fluoro-1-methoxy-4-pentafluorophenylsulfonamidobenzene).
Figure 1B:
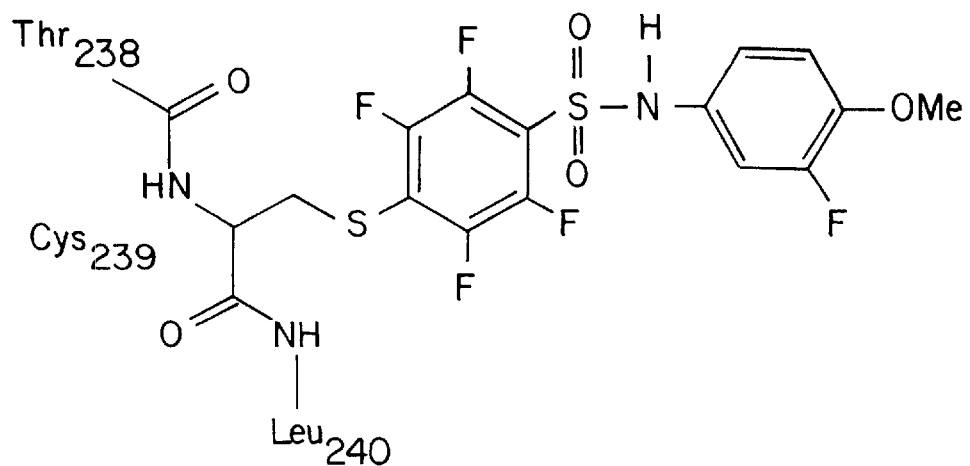
Figure 1C:
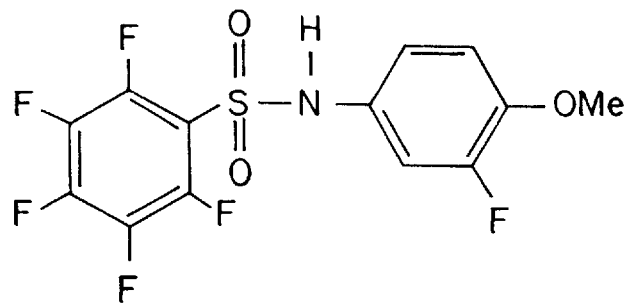

The β-tubulin modifying agent of the invention can be any sulfhydryl or disulfide modifying agent, e.g., one that specifically reacts with the sulfur group on a cysteine residue of a β-tubulin isotype, preferably cysteine residue 239. Preferably, the β-tubulin modifying agents are substituted benzene compounds, pentafluorobenzenesulfonamides, arylsulfonanilide phosphates, and derivatives, analogs, and substituted compounds thereof (see, e.g., U.S. Pat. No. 5,880,151; PCT 97/02926; PCT 97/12720; PCT 98/16781; PCT 99/13759; and PCT 99/16032, herein incorporated by reference). In one embodiment, the agent is 2-fluoro-1-methoxy-4-pentafluorophenylsulfonamidobenzene (compound 1; FIG. 1C).

Preferred monoclonal anti-modified β-tubulin antibodies of the invention include, e.g., 1F6D8, 1B2C11, 3A1C11, 2C1H7, 3F2A4, 5F5C11, and 6D4D11. The antibodies are optionally linked to detectable moieties such as biotin, enzymes, or iodine. In addition to antibodies that specifically bind to modified β-tubulin, the invention also provides control antibodies such as those that bind to both modified and unmodified tubulin. Such antibodies include, e.g., 3D12D1, 4B6G6, 5F1D4, 6H8E3, and 6H10C7. Other control antibodies include those that specifically bind unmodified β-tubulin. Such antibodies include, e.g., 3E10A3, 6A7F9, and 6E7G1.

Anti-modified β-tubulin antibodies are detected using immunoassays of the invention, such as ELISA assays, where the antibody is captured by modified β-tubulin or an immunogenic fragment thereof. In one embodiment, the immunogenic fragments of modified human β2- and β4-tubulin are ATMSGVTTCLRFPGQLNA (SEQ ID NO: 1) or KATMSGVTTCLRFPGQLNA (SEQ ID NO: 3). In another embodiment, the immunogenic fragment of modified human β-1 tubulin is GTMECVTTCLRFPGQLNA (SEQ ID NO: 2). This method is used, e.g., to detect anti-modified β-tubulin antibodies in patient samples such as blood samples, or to titer antibodies of the invention.

The poly- or monoclonal antibodies or their modified derivatives can be used in "real time" imaging technologies to detect the spatial distribution or localization of modified β-tubulin in living higher eukaryotes (e.g., mice, dog, rat, primates or human) exposed to a β-tubulin modifying agent or its tritiated derivative by infusion or bolus injection.

The modified β-tubulin peptide can be used in ELISA or related assays to determine the level of antibodies in the blood of higher eukaryotes that are directed against modified β-tubulin after treatment with β-tubulin modifying agents such as those described herein.

II. Definitions

As used herein, the following terms have the meanings ascribed to them unless specified otherwise.

"Modified β-tubulin or an antigenic fragment thereof" refers to an isotype of β-tubulin, e.g., β1-, β2-, and β4-tubulin, and alleles thereof, which contain a modified amino acid residue, preferably a cysteine residue, preferably the cysteine residue residing at position 239, or a peptide fragment comprising the modified residue, preferably a cysteine residue, preferably the cysteine at position 239. β-tubulin modifying agents that specifically react with the residue to be modified, preferably a cysteine residue, preferably the cystine residue at position 239, are used to make the modified β-tubulin. The agent can be administered to cells or extracts using in vitro experiments (e.g., microtubule polymerization assays), to cultured cells, and to patients via, e.g., infusion or bolus injection. The agent is administered using methods known to those of skill in the art (see, e.g., Example section). Optionally, the agent is labeled with a detectable moiety, e.g., tritiated. Preferably, the β-tubulin peptide is at least about 8 amino acids in length, optionally 10, 15, 18, 19, 20, 25, or more amino acids in length, and is optionally conjugated to a carrier protein. Full length modified β-tubulin is also encompassed by this definition. Prior to modification, the β-tubulin can be synthetic, naturally occurring, or recombinant. The β-tubulin is eukaryotic, typically from a mammal, preferably from a human. Similarly, modified α-tubulin refers to an α-tubulin having a modified amino acid residue.

An "anti-modified β-tubulin" antibody is an antibody or antibody fragment that specifically binds a β-tubulin modified at an amino acid residue, preferably a cysteine residue, preferably the cysteine residue at position 239, or a subsequence thereof comprising the modified amino acid. Similarly, anti-modified α-tubulin" refers to an antibody that specifically binds to an α-tubulin having a modified amino acid residue.

A "β-tubulin modifying agent" refers to an agent that has the ability to specifically react with an amino acid residue of β-tubulin, preferably a cysteine, more preferably the cysteine residue at position 239 of a β-tubulin isotype such as β1- β2- or β4-tubulin and antigenic fragments thereof comprising the residue, preferably cysteine 239. The β-tubulin modifying agent of the invention can be, e.g., any sulfhydryl or disulfide modifying agent known to those of skill in the art that has the ability to react with the sulfur group on a cysteine residue, preferably cysteine residue 239 of a β-tubulin isotype. Preferably, the β-tubulin modifying agents are substituted benzene compounds, pentafluorobenzenesulfonamides, arylsulfonanilide phosphates, and derivatives, analogs, and substituted compounds thereof (see, e.g., U.S. Pat. No. 5,880,151; PCT 97/02926; PCT 97/12720; PCT 98/16781; PCT 99/13759; and PCT 99/16032, herein incorporated by reference; see also Pierce Catalogue, 1999/2000, and Means, *Chemical Modification of Proteins*). In one embodiment, the agent is 2-fluoro-1-methoxy-4-pentafluorophenylsulfonamidobenzene (compound 1; FIG. 1C). Modification of a β-tubulin isotype at an amino acid residue, e.g., cysteine 239, by an agent can be tested by treating a β-tubulin peptide, described herein, with the putative agent, followed by, e.g., elemental analysis for a halogen, e.g., fluorine, reverse phase HPLC, NMR, or sequencing and HPLC mass spectrometry. Optionally compound 1 described herein can be used as a positive control. Similarly, an α-tubulin modifying agent refers to an agent having the ability to specifically modify an amino acid residue of an α-tubulin.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the various immunoglobulin diversity/joining/variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay wherein an antibody specifically binds to an antigen. The immunoassay is characterized by the use of specific binding properties of a particular antibody to isolate, target, and/or quantify the antigen. In addition, an antigen can be used to capture or specifically bind an antibody.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to modified β-tubulin from specific species such as rat, mouse, or human can be selected to obtain only those polyclonal antibodies that are specifically immunoreactive, e.g., with β-tubulin modified at cysteine 239 and not with other proteins. This selection may be achieved by subtracting out antibodies that cross-react with other molecules. Monoclonal antibodies raised against modified β-tubulin can also be used. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

A "label" or a "detectable moiety" is a composition detectable by spectroscopic, photochemical, biochemical, immunochemical, or chemical means. For example, useful labels include $^{32}P$, fluorescent dyes, iodine, electron-dense reagents, enzymes (e.g., as commonly used in an ELISA), biotin, digoxigenin, or haptens and proteins for which antisera or monoclonal antibodies are available, e.g., by incorporating a radiolabel into the peptide.

A "labeled antibody or probe" is one that is bound, either covalently, through a linker or a chemical bond, or noncovalently, through ionic, van der Waals, electrostatic, or hydrogen bonds to a label such that the presence of the antibody or probe may be detected by detecting the presence of the label bound to the antibody or probe.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

III. Preparation of Monoclonal Antibodies

Methods of producing polyclonal and monoclonal antibodies that react specifically with modified β-tubulin are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Antibodies are purified using techniques well known to those of skill in the art.

A number of modified β-tubulin comprising immunogens may be used to produce antibodies specifically reactive with modified β-tubulin isotypes. For example, naturally occurring β-tubulin or an antigenic fragment thereof comprising a residue to be modified, e.g., the cysteine residue at amino acid position 239, is isolated using methods well known to those of skill in the art. Alternatively, synthetic β-tubulin or a synthetic peptide fragment thereof derived from the sequences disclosed herein, optionally conjugated to a carrier protein can be used as an immunogen. In one embodiment, the following peptides are used to produce antibodies specifically reactive with modified β-tubulin: ATMSGVTTCLRFPGQLNA (SEQ ID NO: 1, GTMECVT-TCLRFPGQLNA (SEQ ID NO: 2), and KATMSGVTTCL-RFPGQLNA (SEQ ID NO: 3). Naturally occurring protein may also be used either in pure or impure form. Recombinant protein can also be expressed in eukaryotic or prokaryotic cells, and purified using methods known to those of skill in the art. The β-tubulin is modified with a β-tubulin modifying agent, such as compound 1, and then injected into an animal capable of producing antibodies. Either monoclonal or polyclonal antibodies may be generated, for subsequent use in immunoassays to measure or isolate the protein.

Methods of producing of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to modified β-tubulin. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against unmodified β-tubulin or other proteins, using a competitive binding immunoassay. Specific polyclonal antisera and monoclonal antibodies will usually bind with a $K_d$ of at least about 0.1 mM, more usually at least about 1 $\mu$M, optionally at least about 0.1 $\mu$M or better, and optionally 0.01 $\mu$M or better.

Once modified β-tubulin specific antibodies are available, modified β-tubulin can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

IV. Immunoassays

Modified β-tubulin isotypes, e.g., those modified at cysteine 239, can be detected, isolated, and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the modified β-tubulin or antigenic subsequence thereof). The antibody (e.g., anti-modified β-tubulin) may be produced by any of a number of means well known to those of skill in the art and as described above. For isolation of modified β-tubulin, typically the antibody/antigen complex is dissociated by washing using means known to those of skill in the art. In such applications, typically the antibody is fixed to a substrate such as a plate or a column via covalent or non-covalent linkages (e.g., steptavidin, protein A, protein G, secondary antibodies, and the like). When the assay is used for monitoring and adjusting the dose of β-tubulin modifying agent administered to a patient, a standard curve of known concentrations of modified β-tubulin is prepared, for comparison with test results and for quantitating the amount of modified β-tubulin in the sample. Typically, the standard curve is generated using the same methodology as is used to detect modified β-tubulin in the patient sample, e.g., ELISA, immunoprecipitation, and the like. Preferred immunoassays of the invention include western blots, ELISA, immunoprecipitation, in situ immunohistochemistry, and immunofluorescence assays.

In another embodiment, anti-modified β-tubulin antibodies are detected using immunoassays of the invention, such as ELISA assays, where the antibody is captured by modified β-tubulin or an immunogenic fragment thereof. In one embodiment, the immunogenic fragments are ATMSGVT- TCLRFPGQLNA (SEQ ID NO: 1), GTMECVTTCLRF-PGQLNA (SEQ ID NO: 2), or KATMSGVTTCLRF-PGQLNA (SEQ ID NO: 3).

Samples used for immunoassays can be obtained, e.g., from in vitro microtubule polymerization reactions treated with a β-tubulin modifying agent; tissue culture cells treated with a β-tubulin modifying agent; tissue, blood, or other samples, e.g., tumor samples, from mammalian subjects treated with a β-tubulin modifying agent by, e.g., infusion or injection (e.g., human patients treated with β-tubulin modifying agent chemotherapy).

Immunoassays also often use a labeling agent to specifically bind to and label the complex formed by the antibody and antigen. The labeling agent may itself be one of the moieties comprising the antibody/antigen complex. Thus, the labeling agent may be a labeled modified β-tubulin or a labeled anti-modified β-tubulin antibody. Alternatively, the labeling agent may be a third moiety, such a secondary antibody, that specifically binds to the antibody/modified β-tubulin complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting and/or isolating modified β-tubulin in samples may be either competitive or noncompetitive. Noncompetitive immunoassays are assays in which the amount of antigen is directly measured. In a "sandwich" assay, for example, the anti-modified β-tubulin antibodies can be bound directly to a solid substrate on which they are immobilized. These immobilized antibodies then capture modified β-tubulin present in the test sample. Modified β-tubulin thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety. Methods of binding molecules to a solid support, either covaltently or non-covalently, are well known to those of skill in the art. A variety of solid supports known to those of skill in the art, e.g., plates, columns, dipsticks, membranes, and the like, can be used with the present invention.

Competitive Assay Formats

In competitive assays, the amount of modified β-tubulin present in the sample is measured indirectly by measuring the amount of a known, added (exogenous) modified β-tubulin displaced (competed away) from an anti-modified β-tubulin antibody by the unknown modified β-tubulin present in a sample. In one competitive assay, a known amount of modified β-tubulin is added to a sample and the sample is then contacted with an antibody that specifically binds to modified β-tubulin. The amount of exogenous modified β-tubulin bound to the antibody is inversely proportional to the concentration of modified β-tubulin present in the sample. In one embodiment, the antibody is immobilized on a solid substrate. The amount of modified β-tubulin bound to the antibody may be determined either by measuring the amount of modified β-tubulin present in a modified β-tubulin/antibody complex, or alternatively by measuring the amount of remaining uncomplexed protein. The amount of modified β-tubulin may be detected by providing a labeled modified β-tubulin molecule.

A hapten inhibition assay is another competitive assay. In this assay the known modified β-tubulin, is immobilized on a solid substrate. A known amount of anti-modified β-tubulin antibody is added to the sample, and the sample is then contacted with the immobilized modified β-tubulin. The amount of anti-modified β-tubulin antibody bound to the known immobilized modified β-tubulin is inversely proportional to the amount of modified β-tubulin present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, a polypeptide comprising at least an antigenic subsequence of modified β-tubulin can be immobilized to a solid support. Proteins (e.g., unmodified β-tubulin or β-tubulin isotypes that lack, for example, a cysteine at position 239) are added to the assay that compete for binding of the antisera to the immobilized antigen. The ability of the added proteins to compete for binding of the antisera to the immobilized protein is compared to the ability of modified β-tubulin (e.g., β1, β2, or β4-tubulin or antigenic fragments thereof comprising the cysteine at amino acid 239) to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps a modified β-tubulin, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the immunogen protein that is required to inhibit 50% of binding, then the second protein is said to specifically bind to the polyclonal antibodies generated to a modified β-tubulin immunogen.

Other Assay Formats

Western blot (immunoblot) analysis is used to detect and quantify the presence of modified β-tubulin in the sample.

The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind modified β-tubulin. The anti-modified β-tubulin antibodies specifically bind to the modified β-tubulin on the solid support. These antibodies may be directly labeled or, alternatively, may be subsequently detected using labeled antibodies (e.g., labeled sheep anti-mouse antibodies) that specifically bind to the anti-modified β-tubulin antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize modified β-tubulin, or secondary antibodies that recognize anti-modified β-tubulin.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

V. Kits

The present invention also provides kits for detecting and isolating modified β-tubulin, as well as kits for detecting anti-modified β-tubulin antibodies. For example, such kits can comprise any one or more of the following materials: anti-modified β-tubulin, reaction tubes, and instructions for detecting modified β-tubulin. Optionally, for detection of anti-modified β-tubulin, the kit contains modified β-tubulin peptide. When the kit is used for monitoring and adjusting the dose of a β-tubulin modifying agent administered to a patient, a standard curve of a known concentration of modified β-tubulin can be included in the kit, for comparison with test results and for quantitating the amount of modified β-tubulin in the sample. Typically, the standard curve is generated using the same methodology as is used to detect modified β-tubulin in the patient sample, e.g., ELISA, immunoprecipitation, and the like. A wide variety of kits and components can be prepared according to the present invention, depending upon the intended user of the kit and the particular needs of the user.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

I. Methods

A. Generation of Anti-compound 1-modified β-tubulin Peptide

As an immunogen a peptide derived from human β-tubulin [H]-$A_{231}$TMSGVTTCLRFPGQLNA$_{248}$-[OH]; SEQ ID NO: 1) was synthesized on an lysine residue phase Fmoc chemistry (Fmoc-Ala-Wang-Resin, Midwest Bio-Tech Inc.) with HBTU/HOBT activation, giving a peptide of the following sequence [H]-KATMSGVTTCLRFPGQLNA-[OH] (SEQ ID NO: 3). After completion of the synthesis, the peptide was deprotected and cleaved at room temperature from the solid support using a mixture of 2.5% ethanedithiol, 5% thioanisole, 5% water, 5% phenol, and 82.5% trifluoroacetic acid over a period of 2 hours. The peptide was purified by C18 reverse phase HPLC. After modification of the peptide with compound 1 (see FIG. 1C)under alkaline reaction conditions (pH 8.5) at room temperature, the resulting peptide (FIG. 1a) was purified by reverse phase HPLC. The correct coupling of compound 1 to $Cys_{239}$ was determined by $F^{19}$-NMR-spectroscopy (FIG. 1B).

B. Generation of Monoclonal Antibodies

Monoclonal antibodies were generated by conjugating the compound 1-modified peptide through the amino terminal lysine residue to the carrier protein KLH essential as described by Harlow & Lane, *Antibodies: A Laboratory Manual*, (1988). Spleen cells from immunized Balb/c mice were fused to P3×63.Ag8.653 cells essential as described by Koehler & Milstein *Nature* 256:495–497 (1975) and Harlow & Lane, supra.

C. Generation of Polyclonal Antibodies

The generation of polyclonal antibodies was based on a standard procedure as described in Harlow & Lane, supra.

D. ELISA Assay

ELISA assays were performed under conditions described in Harlow & Lane, with the following modifications. Compound 1-modified β2-tubulin peptide or the unmodified β2-tubulin peptide were conjugated to goat gamma globulin (GGG) through the amino terminal lysine residue. Immulon II 96-well plates were incubated with the conjugate for 30 min at 37° C. before a well was incubated with one particular tissue culture supernatant, derived from a single hybridoma line, at 37° C. for 30 min. Binding of monoclonal antibodies to the substrate was visualized with goat anti mouse IgG conjugated to horseradish peroxidase (HRP) at $OD_{405/490}$.

E. Labeling of Cellular Tubulin in MCF7 and MCF7/ADR Cell with Compound 1 and $^3$H-compound 1, Respectively MCF7/ADR cells ($2\times10^5$ cells) were plated in Dulbecco's Modified Eagle's Medium F12 (DMEM/F12; Mediatech) containing 10% fetal calf serum (FCS) 24 h prior to treatment. Following a 3 h incubation with 800 nM $^3$H-compound 1 (20 Ci/mmol, 1 mCi/ml) at 37° C./5% $CO_2$ cells were harvested by centrifugation (2500 rpm/10 min) and the cell pellet was resuspended in 30 µl of IEF-buffer (9M urea, 2% NP40 (v/v), 200 mM 2-mercaptoethanol) and subsequently mixed with an equal volume of 2×Laemmli SDS-sample buffer. Extracts from untreated cells were prepared in the same manner. Cellular proteins were analyzed by SDS-PAGE by loading 30 µl of the sample per lane (Sambrook, et al., *Molecular cloning: A Laboratory Manual* (1989)). After transfer of the proteins to nitrocellulose membrane, the membrane bound proteins were stained with PonceauS solution. The membrane was then cut in to ten strips of equal size. Western blot analyses was performed essentially as described by Harlow & Lane supra. Tubulin was detected with mouse anti-α/β-tubulin antibody (Biogenex, 1:100 dilution in PBS containing 3% dry milk (w/v), 0.1% Tween 20 (v/v)), whereas $^3$H-compound 1-modified β-tubulin was detected with antibodies directed against compound 1-modified monoclonal antibodies. When monoclonal antibodies were used the tissue culture supernatant was used directly. The membrane was incubated for 12 h at 4° C. with the primary antibodies. The western blots were developed using anti-mouse IgG antibodies conjugated to HRP (1:10,000 in PBS/3% dry milk (w/v), 0.1% Tween 20 (v/v)) and the ECL detection system by incubating the membrane with the secondary antibodies for 1 h at room temperature.

Cellular β-tubulin in MCF7 cells was labeled with 150 nM, 400 nM, 3 µM and 6 µM compound 1 as described above. Cells were harvested at the indicated time points. Cells were lysed and proteins (7.5 µl aliquot) were separated by SDS-PAGE and compound 1-modified β-tubulin was visualized by western blot analyses as outlined above.

F. In Vitro Labeling of Bovine Brain Tubulin with $^3$H-compound 1

Purified bovine brain tubulin (20 µg in BRB80 buffer (80 mM PIPES (pH 6.8), 0.5 mM $MgCl_2$, 1 mM EGTA)/10% glycerol; Cytoskeleton) supplemented with 488 µl of BRB80 buffer was incubated at 37° C. with 10 µCi of $^3$H-compound 1. After 3 h the sample was mixed with 500 µl of BRB80 buffer containing 2M urea. Subsequently the sample was mixed with an equal volume of 2×SDS-sample buffer. A serial dilution of the $^3$H-compound 1-modified β-tubulin was made by mixing an aliquot 1:1, 1:2, 1:4 etc. with 1×SDS-sample buffer containing 10 µl/ml unmodified bovine brain tubulin, resulting in a solution that has the same concentration of α/β-tubulin (10 µg/ml) but various concentrations of compound 1-modified β-tubulin. 100 ng of tubulin solution were resolved by SDS-PAGE and the amount of modified β-tubulin was analyzed by western blotting (see above) or autoradiography of SDS-PAGE. The degree of $^3$H-compound 1-tubulin modification was determined by cutting out the proteins from the gel and measuring the radioactivity in a scintillation counter.

G. Analyses of Blood Samples

White blood cells ("WBC") were isolated from blood samples (5 ml) taken immediately after a 3 h infusion of compound 1 sodium salt from rats or a human patient treated at 20 mg/kg and 220 mg/m$^2$, respectively, as follows. The samples were mixed with 5 ml of PBS and layered on a Ficoll cushion (10 ml, "Lymphoprep" (density is ~1.077 and osmolality 280 mOsm, Gibco/BRL). After centrifugation (1000 rpm, 30 min (Sorvall RC3C centrifuge)) at room temperature WBC were isolated from the cushion and the sample was diluted 1:5 with PBS. After centrifugation (2000 rpm for 10 min) the liquid was discarded and the cell pellet was resuspended in 1 ml of PBS. The solution was transferred to an Eppendorf tube and the cells were collected by centrifugation (3000 rpm, 5 min). After the supernatant was discarded the cell pellet was stored at −80° C. or processed as follows. Rat WBC-pellet was resuspended in 15 µl of IEF-buffer and mixed with 15 µl of 2×SDS sample buffer. The human sample was mixed immediately with an equal volume (10 µl) of SDS sample buffer. Protein samples (2.5 µl, human; 2 µl, rat) were analyzed by SDS-PAGE and subjected to western blot analyzes as outlined above.

As a standard 10 µg of purified brain tubulin was mixed with 489 µl of BRB80 buffer and incubated with 10 µl of $^3$H-compound 1 (10 µCi) in a 500 µl reaction at 377° C. for 2 h. Afterwards the solution was mixed with 500 µl of 2×SDS-sample buffer containing 2 M urea. A 1:1, 1:2 etc. dilution was made by mixing one volume of tubulin solution with 1 volume, 2 volume etc. of 1×SDS-sample buffer. For Western blot analyses 10 μl of sample solution were used.

II. Results

A novel set of seven monoclonal antibodies was generated (FIG. 2) that specifically recognize compound 1-modified β2-tubulin peptides but not unmodified β2-tubulin peptides (FIG. 2A). A second set of five novel monoclonal antibodies specifically recognize the compound 1-modified β2-tubulin peptide as well as its unmodified derivative has been isolated (FIG. 2A). Furthermore, a third class of novel monoclonal antibodies that specifically recognize the unmodified human β2-tubulin peptide was isolated (FIG. 2A). The recognition specificity and the Ig isotypes of the three classes of antibodies is summarized in FIG. 2B.

Figure 3A:
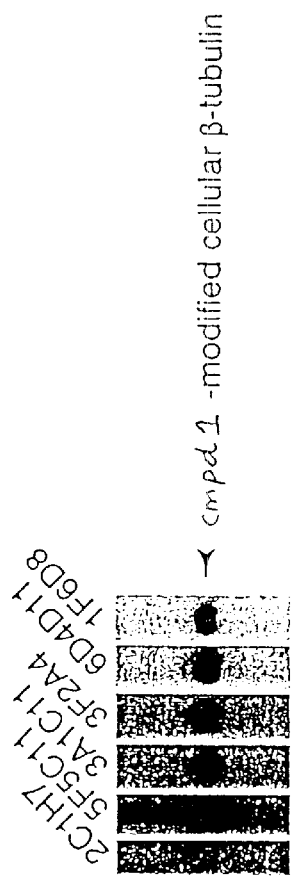
FIG. 3. Antibodies recognize compound 1-modified cellular β-tubulin in MCF7/ADR and MCF7 cells. (A) Antibodies specific to compound 1-modified β-tubulin (see FIG. 1B) recognize compound 1-modified cellular β-tubulin in MCF7/ADR cells treated for 3 hour with 800 nM $^3$H-compound 1 (upper panel), but not unmodified cellular tubulin (lower panel). (B) The monoclonal antibody (2C1H7) can discriminate between different levels of compound 1-modification. Human breast cancer MCF7 cells were treated with 150 nM (lanes 2–5), 400 nM (lanes 6–9), 3 μM (lanes 10–13) and 6 μM (lane 14–17). Cellular protein extracts were prepared at 15 min. (lanes 2, 6, 10, 14), 30 min. (lanes 3, 7, 11, 15), 90 min. (lanes 4, 8, 12, 16) and 180 min. (lanes 5, 9, 13, 17) after adding compound 1 to the cells at the indicated concentrations. Lane 1 shows untreated cellular extract.
Figure 3A:
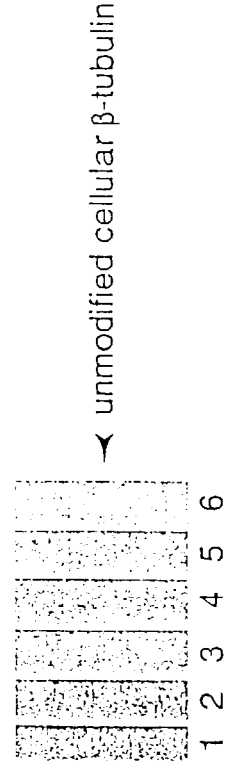

The recognition specificity of the first class of antibodies is not restricted to the compound 1-modified β2-tubulin peptide since they also specifically recognize cellular compound 1-modified β-tubulin. As shown in FIG. 3A, when proteins derived from breast cancer MCF7/ADR cells treated with 800 nM of $^3$H-compound 1, for 3 hours, the monoclonal antibodies (2C1H7, 5F5C11, 3A1C11, 3F2A4, 6D4D11 and 1F6D8) identified a single band, consistent of the size of β-tubulin. When untreated MCF7/ADR cells were used no bands were visible (FIG. 3A). Note that in MCF7/ADR cells the β2- and β4-tubulin isotypes are both labeled, and to a lesser degree, β1-tubulin (Shan et al., supra).

Figure 3B:
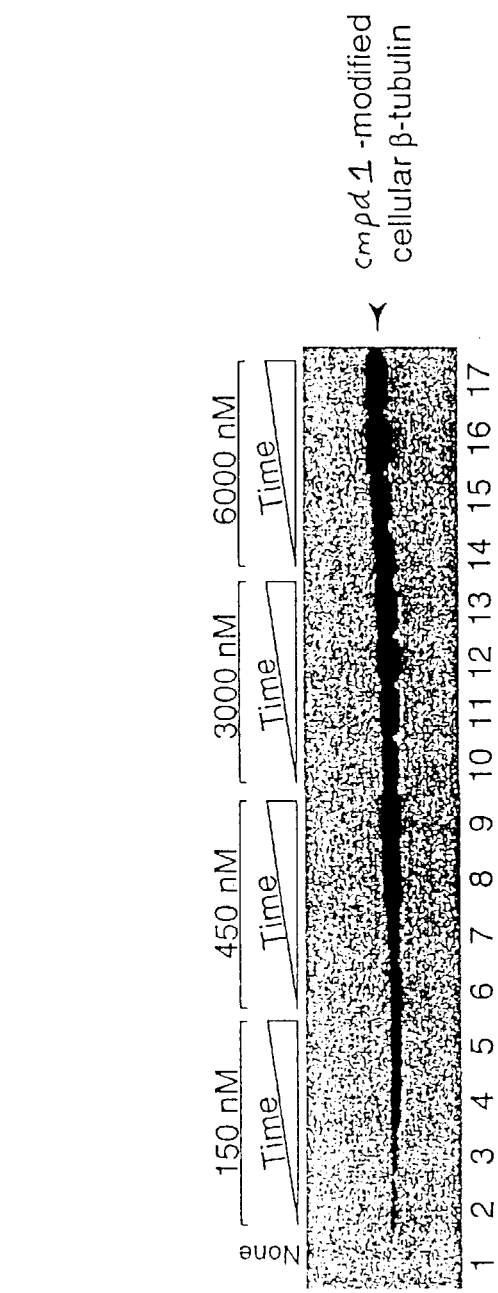

Binding of compound 1 to cellular tubulin is time- and concentration-dependent (Shan et al., supra). To demonstrate that the monoclonal antibodies can monitor different levels of compound 1-modified β-tubulin, human breast cancer MCF7 cells were treated with different concentrations of compound 1 (150 nM, 400 nM, 3 μM and 6 μM). Cells were harvested at 15, 30, 90 and 180 min after the adding compound 1 at the different concentrations to the tissue culture media. Extracted proteins were subjected to western blot analyzes using the monoclonal antibody 2C1H7 (FIG. 1B). As shown in FIG. 3B, the monoclonal antibody 2C1H7 can detect different levels of cellular β-tubulin modification (compare, for example, 90 min treatment at 0.15, 0.4 and 3 μM; lanes 4, 8, and 12, FIG. 3B). The antibody could also discriminate levels of compound 1-modification over time at a constant drug concentration (compare lanes 1 to 5).

Figure 4A:
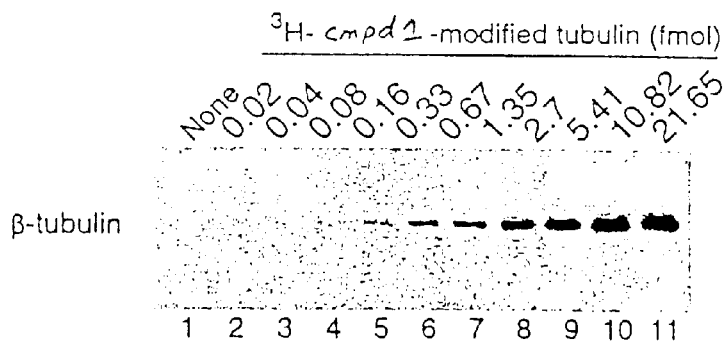
FIG. 4. The monoclonal antibody can discriminate between different levels of $^3$H-compound 1-modified brain β-tubulin. Brain tubulin has been modified in an in vitro reaction with $^3$H-compound 1 (lane 11). Two-fold serial dilution of reaction in lane 11 are shown in lanes 2 to 10. Numbers indicate the concentration of $^3$H-compound 1-modified β-tubulin in each lane. Dilutions of the extract were made so that the concentration of α/β tubulin was the same as in lane 11. Lane 1 contains unmodified brain tubulin. (A) Western blot using an antibody (2C1H7) specific to compound 1-modified β-tubulin. (B) Western blot using an antibody specific to α/β-tubulin. (C) Autoradiogram of SDS-PAGE shown in panel A.
Figure 4B:
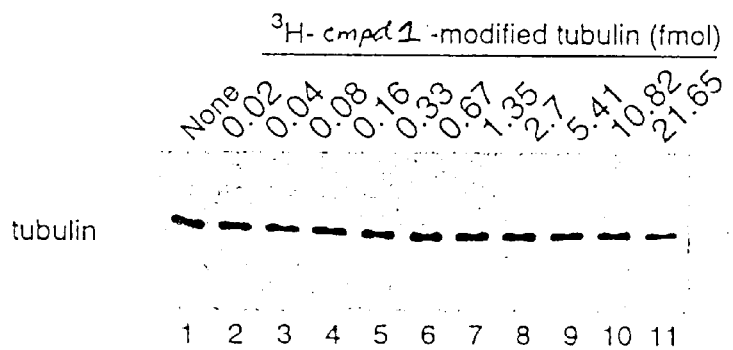
Figure 4C:
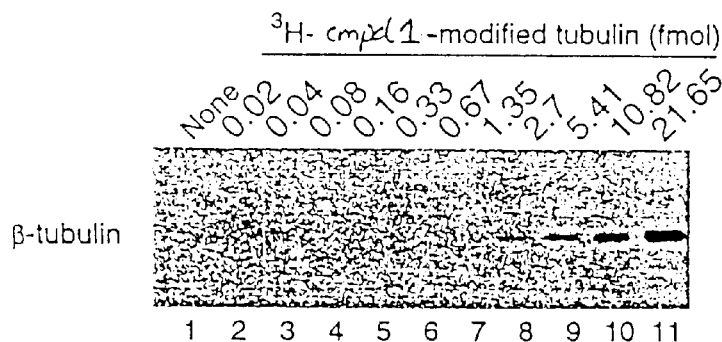

Likewise, when purified brain tubulin was modified with $^3$H-compound 1 in an in vitro reaction, the monoclonal antibody 2C1H7 can discriminate between different levels of compound 1-modified β-tubulin (FIG. 4A–C). Since the radioactivity associated with each protein band was determined the degree of β-tubulin modification by $^3$H-compound 1 was quantitated (FIG. 4A). It is notable that the antibody detection method is significantly more sensitive than the radioactive detection methods (compare FIG. 4A to FIG. 4C). Such a standard curve of a known concentration of compound 1-modified β-tubulin is an essential tool to determine the degree of β-tubulin modification in cells or tissues derived from higher eukaryotes exposed to compound 1.

FIG. 5 shows an example of determining the degree of β-tubulin modification in cells or tissues derived from higher eukaryotes exposed to T13806. White blood cells were isolated from blood derived from rats or a human patient that were exposed to compound 1 or from control groups that were not exposed to compound 1. As shown in FIG. 5A, when proteins derived white blood cells from rats or a human control group (lanes 1 and 3) were subjected to western blot analyzes using the monoclonal 2C1H7 antibody no protein bands were visible. In contrast, when proteins from white blood cells isolated from rats or a human exposed to compound 1 were analyzed a protein consistent of the size of β-tubulin was visible. The results indicate that specific β-tubulin isotype modification can be detected using the monoclonal antibodies.

A comparison of the signal of the human sample with a $^3$H-compound 1—β-tubulin standard curve (FIG. 5B) shows that close to 7.5 fmol of the loaded tubulin is modified by compound 1. This number can be put in perspective by determining the total amount of β-tubulin in these cells. Once this amount is determined it is possible to calculate the total amount of β-tubulin isotypes that are modified by compound 1 relative to the total amount of tubulin. Thus, it is possible to determine how the degree of compound 1-modified β-tubulin changes in response to different compound 1 dose regiments.

What is claimed is:

1. A method of detecting in a sample a β-tubulin isotype modifed at a cysteine residue at amino acid position 239 by treatment with a sulfhydryl or disulfide β-tubulin modifying agent, the method comprising the steps of:

(a) providing a sample treated with the β-tubulin modifying agent;

(b) contacting the sample with an antibody that specifically binds to the β-tubulin isotype modified at the cysteine residue at amino acid position 239; and (c) determining whether the sample contains the β-tubulin isotype modified at the cysteine residue at amino acid position 239 by detecting the antibody.

2. The method of claim 1, wherein the antibody is a monoclonal antibody.

3. The method of claim 1, wherein the antibody is 2C1H7 (ATCC Accession Number PTA-2686).

4. The method of claim 1, further comprising the step of using a control antibody that recognizes both the β-tubulin isotype modified at the cysteine residue at amino acid position 239 and an unmodified β-tubulin isotype.

5. The method of claim 1, further comprising the step of using a control antibody that recognizes only a β-tubulin isotype that is not modified at the cysteine residue at amino acid position 239.

6. The method of claim 1, wherein the step of determining whether the sample contains the β-tubulin isotype modified at the cysteine residue at amino acid position 239 comprises detecting the antibody in an assay selected from the group consisting of an ELISA assay, a western blot, an immunohistochemical assay, an immunofluorescence assay, and a real time imaging assay.

7. The method of claim 1, wherein the step of determining whether the sample contains the β-tubulin isotype modified at the cysteine residue at amino acid position 239 further comprises quantitating the amount of the β-tubulin isotype in the sample.

8. The method of claim 1, wherein the antibody is bound to a solid substrate.

9. The method of claim 1, wherein the sample is selected from the group consisting of an in vitro tubulin polymerization reaction sample, a cultured cell, and a patient sample.

10. The method of claim 9, wherein the patient sample is a blood sample.

11. The method of claim 9, wherein the patient sample is from a cancer patient receiving pentafluorobenzenesulfonamide chemotherapy.

12. The method of claim 9, wherein the patient sample is from a cancer patient receiving 2-fluoro-1-methoxy-4-pentafluorophenylsulfonamidobenzene chemotherapy.

13. The method of claim 9, wherein the patient sample is from a human patient.

14. The method of claim 1, wherein the antibody is covalently linked to a detectable moiety.

15. The method of claim 14, wherein the antibody is covalently linked to a biotin moiety, an iodine moiety, or an enzyme moiety.

16. A method of detecting in a sample a tubulin isotype modified at a cysteine residue, at amino acid position 239 the isotype modified by treatment with a sulfhydryl or a disulfide tubulin modifying agent, comprising the steps of:
   (a) providing a sample treated with the tubulin modifying agent;
   (b) contacting the sample with an antibody that specifically binds to the tubulin isotype modified at a cysteine residue at amono acid position 239; and
   (c) determining whether the sample contains the tubulin isotype modified at a cysteine residue at amino acid position 239 by detecting the antibody.

17. A method of monitoring the amount of a tubulin modified at a cysteine residue at amino acid position 239 in a patient treated with a sulfhydryl or a disulfide tubulin modifying agent, the method comprising the steps of:
   (a) providing a sample from the patient treated with the tubulin modifying agent;
   (b) contacting the sample with an antibody that specifically binds to the tubulin modified at a cysteine residue at amino acid position 239; and
   (c) determining the amount of the tubulin modified at a cysteine residue at amino acid position 239 in the patient sample by detecting the antibody and comparing the amount of antibody detected in the patient sample to a standard curve, thereby monitoring the amount of the tubulin modified at a cysteine residue at amino acid position 239 in the patient.

* * * * *

SEQUENCE LISTING

<160> NUMBER OF SEQ ID NOS: 4

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence:immunogenic
      fragment of modified beta2 and beta4 tubulin

<400> SEQUENCE: 1

Ala Thr Met Ser Gly Val Thr Thr Cys Leu Arg Phe Pro Gly Gln Leu
 1               5                  10                  15

Asn Ala

<210> SEQ ID NO 2
<211> LENGTH: 18

```
-continued

<212> TYPE: PRT
<213> ORGANISM: Artificial Sequence
<220> FEATURE:
<223> OTHER INFORMATION: Description of Artificial Sequence:immunogenic
      fragment of modified beta1 tubulin

<400> SEQUENCE: 2

Gly Thr Met Glu Cys Val Thr Thr Cys Leu Arg Phe Pro Gly Gln Leu
 1               5                  10                  15

Asn Ala

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:immunogenic
      fragment of modified beta2 and beta4 tubulin with
      Lys from lysine residue phase Fmoc chemistry

<400> SEQUENCE: 3

Lys Ala Thr Met Ser Gly Val Thr Thr Cys Leu Arg Phe Pro Gly Gln
 1               5                  10                  15

Leu Asn Ala

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:immunogenic
      fragment of modified beta2 and beta4 tubulin with
      Lys from lysine residue phase Fmoc chemistry
      modified by compond 1
<220> FEATURE:
<221> NAME/KEY: MOD_RES
<222> LOCATION: (10)
<223> OTHER INFORMATION: Xaa = Cys modified by compound 1
      (2-fluoro-1-methoxy-4-pentafluorophenylsulfonamido
      benzene)

<400> SEQUENCE: 4

Lys Ala Thr Met Ser Gly Val Thr Thr Xaa Leu Arg Phe Pro Gly Gln
 1               5                  10                  15

Leu Asn Ala
```